United States Patent [19]

Faucher et al.

[11] 4,018,729

[45] Apr. 19, 1977

[54] SHAPED ARTICLE FOR CONDITIONING HAIR A BLEND OF WATER-SOLUBLE AND WATER-INSOLUBLE POLYMERS WITH INTERPENETRATING NETWORKS

[75] Inventors: Joseph A. Faucher, Pleasantville; Meyer Robert Rosen, Spring Valley, both of N.Y.

[73] Assignee: Union Carbide Corporation, New York, N.Y.

[22] Filed: Nov. 10, 1975

[21] Appl. No.: 630,404

Related U.S. Application Data

[62] Division of Ser. No. 510,998, Oct. 1, 1974, Pat. No. 3,992,336.

[52] U.S. Cl. .................................. 260/17 R; 132/7; 132/11 R; 132/40; 132/42 R; 132/136; 132/163; 260/13; 260/823; 260/874; 260/895; 260/897 R

[51] Int. Cl.² ................... A45D 24/00; A61K 7/06; C08L 1/28

[58] Field of Search .......... 260/823, 874, 895, 897, 260/13, 17 R; 132/7, 11 R, 163, 136, 40, 42 R

[56] References Cited

UNITED STATES PATENTS

| | | | |
|---|---|---|---|
| 2,577,921 | 12/1951 | Samel et al. | 132/163 |
| 3,346,457 | 10/1967 | Dasher | 424/80 |
| 3,472,840 | 10/1969 | Stone et al. | 260/231 |
| 3,715,428 | 2/1973 | Quasius et al. | 132/7 |

FOREIGN PATENTS OR APPLICATIONS

| | | | |
|---|---|---|---|
| 1,144,878 | 3/1963 | Germany | 132/7 |

*Primary Examiner*—Edward M. Woodberry
*Attorney, Agent, or Firm*—Bernard Francis Crowe

[57] ABSTRACT

Articles for conditioning hair have been fabricated by blending water soluble polymers with water insoluble polymers to form interpenetrating networks so that the water soluble polymer can be extracted from the article when wet or when brought in contact with wet hair.

28 Claims, No Drawings

SHAPED ARTICLE FOR CONDITIONING HAIR A BLEND OF WATER-SOLUBLE AND WATER-INSOLUBLE POLYMERS WITH INTERPENETRATING NETWORKS

This is a division of Ser. No. 510,998 filed Oct. 1, 1974 now U.S. Pat. No. 3,992,336.

BACKGROUND OF THE INVENTION

This invention pertains to shaped articles for conditioning hair and more particularly to those fabricated from a blend of a normally solid water soluble organic polymer with a normally solid water insoluble organic polymer.

Aerosol hair sprays have been widely used for conditioning and controlling hair by depositing a polymer thereon. However in recent years aerosol products in general have come under close scrutiny because of possible toxic effects on humans. It is therefore desirable to develop an alternate method of applying hair control agents to hair.

STATEMENT OF THE INVENTION

It has now been found that hair control agents can be applied to hair from shaped articles comprising a blend of a normally solid water soluble organic polymer with a normally solid water insoluble organic polymer in which the two polymers are present in an interpenetrating network. This conditioning of hair can be effected by either wetting the hair before contact with the article or by wetting the article.

DESCRIPTION OF THE INVENTION

The choice of water soluble organic polymer is not narrowly critical but it is preferred to employ water soluble cellulose derivatives, particularly quaternary nitrogen-containing cellulose polymers, hydroxypropyl cellulose and hydroxyethyl cellulose, hydroxyalkyl alkali metal carboxylalkyl cellulose derivatives, and free acid hydroxyalkyl carboxyalkyl cellulose derivatives, as well as vinylpyrrolidone homopolymers and copolymers, polycarboxylic acid derivatives, vinyl methyl ether homopolymers and copolymers, ethylene oxide resins, and the like.

The quaternary nitrogen containing cellulose ethers (hereinafter referred to as QNCC ethers) which can be used in compositions of this invention are those described in U.S. Pat. No. 3,472,840 granted to Stone et al. on Oct. 14, 1969.

The preferred cellulose ether derivative from which the quaternary nitrogen containing cellulose ethers described above are prepared include those which are water soluble, non-ionic, lower alkyl or hydroxy alkyl substituted. Such derivatives include methyl cellulose, ethyl cellulose, and hydroxyethyl cellulose.

A particularly efficacious quaternary nitrogen-substituted cellulose derivative for the purpose of this invention is available from Union Carbide under the code designation "Polymer JR". This polymer has a molecular weight within the range of from 100,000 to 3,000,000. Polymer JR is a cationic cellulose ether have the structure:

wherein $R_{Cell}$ is a residue of an anhydroglucose unit, wherein Y is an integer having values from 50 to 20,000 and wherein each R individually represents a substituent of the general formula:

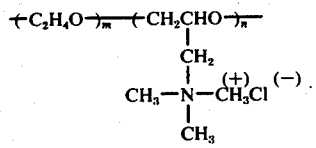

wherein the $m$ is an integer having values from 0 to 10, $n$ is an integer having values from 0 to 3, and $p$ is an integer having values from 0 to 10. The average values per anhydroglucose unit are: $n$ is from 0.35 to 0.45 and the sum of $m$ plus $p$ is from 1 to 2.

The preferred QNCC ethers for use in the practice of the instant invention are those having viscosities of 50 to 35,000 centipoises (cps.) at 25° C in 2% by weight aqueous solutions, when measured by ASTM D-2364-65 (Model LVF Brookfield, 30 rpm Spindle No. 2). QNCC ethers which are particularly useful in the practice of this invention are those sold by Union Carbide Corporation under the trade designation JR-125, JR-400, and JR-30M, signifying a polymer of the type described having viscosities of 1 to 5 cps., 400 cps. and 30,000 cps., respectively.

The term "ethylene oxide resins" as used in the instant invention encompasses not only the homopolymer, poly(ethylene oxide) but also copolymers of ethylene oxide in which ethylene oxide is copolymerized with other alkylene oxides such as propylene oxide, butylene oxide, styrene oxide and the like and other comonomers copolymerizable with ethylene oxide.

Examples of hydroxyalkyl carboxyalkyl celluloses include hydroxyethyl carboxymethyl cellulose, hydroxyethyl carboxyethyl cellulose, hydroxymethyl carboxymethyl cellulose, hydroxypropyl carboxymethyl cellulose, hydroxypropyl carboxyethyl cellulose, hydroxypropyl carboxypropyl cellulose, hydroxybutyl carboxymethyl cellulose, and the like. The preferred alkali metal salts of these hydroxyalkyl carboxyalkyl celluloses are the sodium and the potassium derivatives.

Vinylpyrrolidone and methyl vinyl ether polymers are available from GAF Corporation.

Cationic acrylic acid polymers are available from Hercules Corporation under the trade designation Reten 210 and the like.

The only restriction as to the normally solid water soluble organic polymer components of this invention is that they be incompatible with the water insoluble polymer components thus facilitating the formation of interpenetrating networks in the composite blend.

Representative examples of water insoluble polymers include low density polyethylene, high density polyethylene, polyalkyl acrylates, polyalkyl methacrylates, polystyrene, impact polystyrene, poly(epsilon-caprolactone), vinyl chloride polymers including homopolymers and copolymers of vinyl chloride with such comonomers as ethylene, vinyl acetate and vinyl alcohol, polypropylene, polybutylene, and the like.

In the practice of this invention the water soluble and water insoluble polymers do not form composites wherein discrete particles of the former are embedded in a continuous matrix of the latter but rather a continuous network of the polymers is formed in the blending operation. This is important because it provides a continuous feeding of the water soluble polymer to the surface of the hair treating article which is not possible in a system where the water soluble polymer is embedded as discrete particles.

The amounts of the two polymers in the composite is not narrowly critical and so it is possible to have a range as broad as 1:99 of the water soluble polymer to 99:1 of the water insoluble polymer. However it is preferred to use about 10 to 40 percent by weight of the water soluble polymer present in the shaped article.

Any fabricating method can be used known to those skilled in the art, such as, compression or injection molding. The most useful form of the shaped article is a comb or a brush in which the bristles contain the polymer blend. However one can also use hair curlers where the surface or all of the curler is fabricated from the polymer blend. Exact molding temperatures and pressures will vary with the particular polymers used but again this is within the expertise of those skilled in the art.

It will be understood that minor amounts of additives can be included in the polymer blends of this invention such as colorants, dyes, antistatic agents, antioxidants, heat and ultraviolet stabilizers and the like.

It will be apparent to users of this invention that it can be practiced by wetting either the hair or the hair conditioning article or both with water prior to contact.

As a variation of this invention the hair conditioning article can be fabricated from a composite of a normally solid polymer which is soluble in a lower non-toxic alcohol such as ethanol or isopropanol, and a normally solid polymer which is insoluble in these alcohols. The article can be used by first dipping it into the alcohol or aqueous solutions of the alcohol, and then contacting the hair with the alcohol-wetted article or by wetting the hair with alcohol and then applying the article. Combs, brushes and curlers are also examples of useful articles which can be used in this application technique. If desired the whole hair conditioning article need not be fabricated from the two polymer composite. For example a comb could be made having only the teeth as the polymer composite and the backbone or handle made from any other water insoluble material of construction either polymeric, cellulosic or metallic. The same applies to hair brushes where only the bristles need be fabricated from the polymer composite and the handle can be any other material. This principle of design also applies to hair curlers where only those surfaces in contact with the hair have to be made from the polymer composite.

Although many of the known water and alcohol soluble polymers can be molded into shaped articles without the addition of water insoluble polymers, they are not practical for treating hair because they tend to become slippery due to absorption of water and lose their rigidity. Other water soluble polymers are too rigid in the melt state to provide a satisfactory molding material alone. Polymer JR falls into this category. By blending the two classes of polymers into an interpenetrating network these difficulties are overcome and in addition the resultant composite functions to provide controlled release of the hair active component, viz., a water soluble polymer.

The invention is further described in the Examples which follow. All parts and percentages are by weight unless otherwise specified.

EXAMPLE 1

Since the efficiency of a comb for treating hair depends on the extractability of a polymer from the comb by the action of water, preliminary tests were performed by molding a test comb containing the two classes of polymers described above and placing it in a two quart jar filled with water. A magnetic stir bar was placed in the bottom of the jar and the jar placed on a magnetic stirrer. The comb was left in the jar for a period of days with stirring, removed, dried to constant weight in a 50° C. oven and the weight recorded. In this way one can judge how easily removable the water-soluble polymer is from the composite. Thus for example a comb was molded from a blend of 75 percent by weight of poly(epsilon-caprolactone) and 25 percent by weight of Polymer JR-125. Over 90 percent of the Polymer JR-125 was extracted into the water phase in 21 days. The molding temperature for the fabrication of this comb was about 230°–250° F. (110–123° C.). This high extraction is proof that Polymer JR-125 exists in the form of an interpenetrating network with the poly(epsilon-caprolactone) and not as discrete particles.

EXAMPLE 2

Example 1 was repeated using 20 percent by weight of Polymer JR-125 with 80 percent by weight of high density polyethylene using a molding temperature for the comb of about 320°–360° F. (160–177° C.). About 15 percent of the Polymer JR-125 was absorbed into the water phase in about 1.5 days.

EXAMPLE 3

Example 1 was repeated using 80 percent by weight of poly(epsilon-caprolactone) and 20 percent by weight of polyethylene oxide (POLYOX WSR-301 having a molecular weight of about 3.5 million). About 40 percent by weight of the polyox was extracted into the water phase in about 24 days.

EXAMPLE 4

Example 1 was repeated with the exception that the comb was fabricated from 80 percent poly(epsilon-caprolactone) and 20 percent polyvinylpyrrolidone (having a Fikentscher K value of about 26–28). About 44 percent by weight of the polyvinylpyrrolidone was extracted into the water phase in about 25 days.

EXAMPLE 5

Example 1 was repeated with the exception that the comb was fabricated from 80 percent by weight of poly(epsilon-caprolactone) and 20 percent by weight of Klucel M (a grade of hydroxypropyl cellulose sold by Hercules, Inc. having a molecular weight of about 500,000). About 49 percent by weight of the Klucel M was extracted into the water phase in about 25 days.

EXAMPLE 6

Example 1 was repeated with the exception that the comb was fabricated from 80 percent by weight of poly(epsilon-caprolactone) and 20 percent by weight of Reten 210 (a cationic acrylic acid polymer sold by Hercules Company). About 25 percent by weight of the Reten 210 was extracted into the water phase in about 10 days.

EXAMPLE 7

A panel of 18 people was polled for their response to the use of combs prepared as in Example 1 from a composite of poly(epsilon-caprolactone) and Polymer JR-125 containing 20 percent and 30 percent by weight loadings of the latter respectively. Fifteen out of the eighteen people paneled were favorably impressed when they used the combs by combing their wet hair. They cited improved ease of combing and better control of hair after use. They found there was less "flyaway" experienced when using the combs fabricated as described above as opposed to conventional combs containing no water soluble polymer.

Although the invention has been described in its preferred forms with a certain degree of particularity, it is understood that the present disclosure of the preferred forms has been made only by way of example and that numerous changes may be resorted to without departing from the spirit and the scope of the invention.

What is claimed is:

1. Shaped hair treating article which comprises a blend of a normally solid, water soluble organic polymer selected from the group consisting of ethylene oxide resins, polyvinyl-pyrrolidone, hydroxypropyl cellulose, a cationic polyacrylic acid and polyvinyl methyl ether, in combination with a normally solid, water insoluble organic polymer, selected from the group consisting of polystyrene, poly(epsilon-caprolactone), polyvinyl chloride, a copolymer of vinyl chloride and vinyl acetate, a copolymer of vinyl chloride and ethylene, polypropylene and polybutylene, in which said polymers are present in an interpenetrating network in a ratio of 99:1 to 1:99.

2. Article claimed in claim 1 wherein the water soluble polymer is an ethylene oxide resin.

3. Article claimed in claim 1 wherein the ethylene oxide resin is the homopolymer, poly(ethylene oxide).

4. Article claimed in claim 1 wherein the water soluble polymer is polyvinylpyrrolidone.

5. Article claimed in claim 1 wherein the water soluble polymer is hydroxypropyl cellulose.

6. Article claimed in claim 1 wherein the water soluble polymer is a cationic polyacrylic acid.

7. Article claimed in claim 1 wherein the water soluble polymer is polyvinyl methyl ether.

8. Article claimed in claim 1 wherein the water insoluble polymer is polystyrene.

9. Article claimed in claim 1 wherein the water insoluble polymer is poly(epsilon-caprolactone).

10. Article claimed in claim 1 wherein the water insoluble polymer is polyvinyl chloride.

11. Article claimed in claim 1 wherein the water insoluble polymer is a copolymer of vinyl chloride and vinyl acetate.

12. Article claimed in claim 1 wherein the water insoluble polymer is a copolymer of vinyl chloride and ethylene.

13. Article claimed in claim 1 wherein the water insoluble polymer is polypropylene.

14. Article claimed in claim 1 wherein the water insoluble polymer is polybutylene.

15. Method of conditioning hair which comprises the steps of:
 a. fabricating a hair conditioning shaped article from a blend of a normally solid, water soluble organic polymer and a normally solid water insoluble organic polymer in which said polymers are present in an interpenetrating network in a ratio of 99:1 to 1:99;
 b. wetting the hair with water; and
 c. contacting the wet hair with said hair conditioning article.

16. Method claimed in claim 15 wherein the article is shaped in the form of a comb.

17. Method claimed in claim 15 wherein the article is shaped in the form of a hair curler.

18. Method claimed in claim 15 wherein the article is shaped in the form of a hair brush.

19. Method claimed in claim 15 wherein the water soluble polymer is an ethylene oxide resin.

20. Method claimed in claim 19 wherein the ethylene oxide resin is poly(ethylene oxide).

21. Method claimed in claim 15 wherein the water soluble polymer is polyvinylpyrrolidone.

22. Method claimed in claim 15 wherein the water soluble polymer is a quaternary nitrogen-containing cellulose ether having the structure:

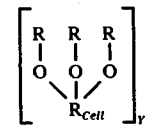

wherein $R_{Cell}$ is a residue of an anhydroglucose unit, wherein Y is an integer having values of from 50 to 20,000 and wherein each R individually represents a substituent of the general formula:

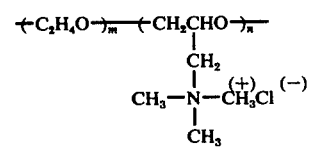

wherein m is an integer having values from 0 to 10, n is an integer having values from 0 to 3 and p is an integer having values from 0 to 10.

23. Method claimed in claim 15 wherein the water soluble polymer is hydroxypropyl cellulose.

24. Method claimed in claim 15 wherein the water soluble polymer is a cationic polyacrylic acid.

25. Method claimed in claim 15 wherein the water soluble polymer is polyvinyl methyl ether.

26. Method of conditioning hair which comprises the steps of:
 a. fabricating a hair conditioning shaped article from a blend of a normally solid water soluble organic polymer and a normally solid water insoluble organic polymer in which said polymers are present in an interpenetrating network in a ratio of 99:1 to 1:99;
 b. wetting said hair conditioning article with ethanol or isopropanol; and
 c. contacting the hair with the wet hair conditioning article.

27. Method of conditioning hair which comprises the steps of:
a. fabricating a hair conditioning shaped article from a blend of a normally solid water soluble organic polymer and a normally solid water insoluble organic polymer in which said polymers are present in an interpenetrating network in a ratio of 99:1 to 1:99.
b. wetting said hair conditioning article with water; and
c. contacting the hair with the wet hair conditioning article.

28. Method of conditioning hair which comprises the steps of:
a. fabricating a hair conditioning shaped article from a blend of a normally solid water soluble organic polymer and a normally solid water insoluble polymer in which said polymers are present in an interpenetrating network in a ratio of 99:1 to 1:99;
b. wetting said hair with ethanol or isopropanol; and
c. contacting the wetted hair with the hair conditioning article.

* * * * *